(12) United States Patent
Sourovoi et al.

(10) Patent No.: US 6,458,381 B1
(45) Date of Patent: Oct. 1, 2002

(54) LIPIDS AND THEIR USE, FOR EXAMPLE, IN LIPOSOMES

(75) Inventors: Andrej Sourovoi, Ul Tverskaya 15-162, 103009 Moscow (RU); Guenther Jung, Tübingen (DE)

(73) Assignee: Andrej Sourovoi, Moscow (RU)

( * ) Notice: Subject to any disclaimer, the term of this patent is extended or adjusted under 35 U.S.C. 154(b) by 0 days.

(21) Appl. No.: 09/125,138

(22) PCT Filed: Feb. 12, 1997

(86) PCT No.: PCT/EP97/00629

§ 371 (c)(1),
(2), (4) Date: Oct. 14, 1998

(87) PCT Pub. No.: WO97/30024

PCT Pub. Date: Aug. 21, 1997

(30) Foreign Application Priority Data

Feb. 13, 1996 (DE) .......................................... 196 05 175

(51) Int. Cl.[7] .............................................. A61K 9/127
(52) U.S. Cl. ......................... 424/450; 564/291; 935/54
(58) Field of Search ................ 424/450, 1.21, 424/9.32, 9.51, 417, 94.3; 935/54; 564/291; 514/642, 2; 451/829; 264/4.1, 4.3, 4.6

(56) References Cited

U.S. PATENT DOCUMENTS

| 4,229,360 | 10/1980 | Schneider et al. |
| 4,235,871 | 11/1980 | Papahadjopoulos et al. |
| 4,241,046 | 12/1980 | Papahadjopoulos et al. |
| 5,208,036 | 5/1993 | Eppstein et al. |

FOREIGN PATENT DOCUMENTS

| EP | 0 187 702 A1 | 7/1986 | ............ C07C/93/02 |
| EP | 0 326 974 A1 | 2/1988 | ............ C07K/5/06 |
| JP | 60228564 A | 11/1985 | ............ B01J/20/26 |
| JP | 60228564 | 11/1985 | ............ B01J/20/26 |
| JP | 61037892 A | 2/1986 | ............ C08K/3/38 |
| JP | 61037892 | 2/1986 | ............ C08K/3/38 |
| JP | 02135092 | 5/1990 | ......... C07C/370/14 |
| JP | 02135092 A | 5/1990 | ......... C07C/370/14 |
| JP | 06340598 A | 12/1994 | ......... C07C/219/06 |

(List continued on next page.)

OTHER PUBLICATIONS

Behr et al., *Proc. Natl. Acad. Sci.*, U.S.A., 86:6982–6986 (1989).
Cotten et al., *Proc. Natl. Acad. Sci.*, U.S.A., 87:4033–4037 (1990).
Cristiano et al., *Proc. Natl. Sci.*, U.S.A., 90:2122–2126 (1993).
Debs et al., *J. Biol. Chem.*, 265:10189–10193 (1990).
Felgner et al., *Proc. Natl. Acad. Sci.*, U.S.A., 84:7413–7417 (1987).

(List continued on next page.)

*Primary Examiner*—Gollamudi S. Kishore
(74) *Attorney, Agent, or Firm*—Leon R. Yankwich; Daivd G. O'Brien

(57) ABSTRACT

The invention concerns novel lipid compounds suitable for the transport of biologically active substances or molecules in cells. A preferred compound according to the invention is L-lysine-bis-(O,O'-cis-9-octadecenoyl-β-hydroxyethyl)-amide dihydrochloride or one of its optical isomers. In addition, the invention concerns complexes of the novel lipid compounds with polyanions such as DNA and RNA, and ternary complexes of the novel lipid compounds with polyanion and polycations. Finally, the invention concerns liposome formulations made from biologically active substances and the novel lipid compounds, as well as methods of transporting polyanions, polycations or biologically active substances through biological membranes by means fo the novel lipid compounds.

52 Claims, 3 Drawing Sheets

FOREIGN PATENT DOCUMENTS

| | | | |
|---|---|---|---|
| WO | WO 89/08098 | 9/1989 | ............ C07C/87/34 |
| WO | WO 91/09837 | 7/1991 | .......... C07C/271/22 |
| WO | WO 93/19768 | 10/1993 | .......... A61K/37/00 |
| WO | WO 95/17373 | 6/1995 | ......... C07C/211/63 |
| WO | WO 95/18863 | 7/1995 | ............ C12N/15/87 |
| WO | WO 96/01840 | 1/1996 | ............ C07K/5/06 |
| WO | WO 96/01841 | 1/1996 | ............ C07K/5/06 |
| WO | WO 96/10390 | 4/1996 | .......... A61K/9/127 |

OTHER PUBLICATIONS

Gao and Huang, *Biochem. Biophys. Res. Commun.*, 179:280–285 (1991).
Huckett et al., *Biochem. Pharmacol.*, 40:253–263 (1990).
Hwu and Rosenberg, *Cancer Detect. Prevent.*, 18:43–50 (1994).
Kerr and Mule, *J. Leucocyte Biol.*, 56:210–214 (1994).
Kunio et al., *Chemical Abstracts*, 114:9 (1991).
Kunitake et al., *Memoirs of Faculty of Engineering, Kyushu University*, 46: 221–243 (1986).
Legendre and Szoka Jr., *Proc. Natl. Acad. Sci., U.S.A.*, 90:893–897 (1993).
Leventis and Silvius, *Biochimica et Biophysica Acta*, 124–132 (1990).
Life Technologies Inc., *CellFectin Reagent and Protocol*, 1–2 (1994).
Malone et al., *Proc. Natl. Acad. Sci., U.S.A.*, 86:6077–6081 (1989).
Nabel et al., *Proc. Natl. Acad. Sci., U.S.A.*, 90:11307–11311 (1993).
Plank et al., *Bioconjugate Chem.*, 533–539 (1992).
Promega Inc., *Technical Bulletin*, 216:1–8 (1995).
Rosenfeld et al. *Cell*, 68:143–155 (1992).
Shirahama et al., *ACS Symp. Ser.*, 311:270–282 (1986).
Szoka and Papahadjiopoulos, *Ann. Rev. Biophys. Bioeng.*, 9:467–508 (1980).
Wagner et al., *Proc. Natl. Acad. Sci., U.S.A.*, 89:6099–6103 (1992).
Wu and Wu, *J. Biol. Chem.*, 262:4429–4432 (1987).
Zhu et al., *Science*, 261:209–211 (1993).

LIPIDS AND THEIR USE, FOR EXAMPLE, IN LIPOSOMES

This application is a 371 of PCT/EP97/00629 filed in Feb. 12, 1997.

This invention relates to lipid compounds and their use, for example for the transport of biologically active substances or molecules in cells.

Liposomes are spherical, self-closed structures composed of lipid bilayers which entrap in their interior a portion of the solvent, in which they float. They may consist of one or more concentric membranes, and their size ranges from several nanometers to several dozens of micrometers.

Liposomes are mostly made from amphiphilic molecules which can be characterized by having a hydrophilic (often named the polar head) and a hydrophobic group (nonpolar tail) on the same molecule. In most cases, liposome-forming molecules are not soluble in water. However, under certain circumstances, they form colloidal dispersions.

Liposomes can be large or small and may be composed from one to several hundred of concentric bilayers. With respect to the size and the nature of the layer (lamellae), they can be classified as multi-lamellar vesicles (MLVs), small uni-lamellar vesicles (SUVs) and large uni-lamellar vesicles LUVs).

SUVs have a diameter from 20 to 600 nm and consist of a single lipid bilayer which surrounds the interior aqueous compartment. LUVs have a diameter from 600 to 30000 nm. MLVs vary greatly in size for up to 10000 nm and contain more than one lipid bilayer, therefore they are multi-compartmental in their structure.

Liposomes can be produced in a number of ways. The so-called "thin-film hydration" method results in the formation of heterogeneous dispersions of predominantly MLVs. By using charged lipid compositions rather high fractions of LUVs can be produced. Said dispersions can be further treated (mechanically, electrostatically or chemically) in order to produce solutions of SUVs. Most frequently these methods include extrusion through filters with pores of different diameter, or sonication.

Alternatively, liposomes can be prepared by lyophilization, where the lipid-film is then dissolved in a volatile solvent (for example tert-butyl alcohol), frozen and lyophilized.

A variety of methods for preparing liposomes have been described in the periodical and patent literature: Szoka and Papahadjopoulos in: Ann. Rev. Biophys. Bioeng. 9, 467–508 (1980) as well as U.S. Pat. Nos. 4,229,360, 4,241,046, 4,235,871.

The most important liposome feature is their ability to dissolve, protect and carry hydrophilic or hydrophobic molecules. For negatively charged drugs, including some proteins, positively charged liposomes can be used. Improvements in therapy were observed, despite the known fact that positively charged liposomes can be toxic.

Various DNA transfection methods have been developed in the past twenty years. These methods include the calcium phosphate precipitation method, DEAE-dextran method, electroporation method, microinjection, receptor mediated endocytosis, liposomes and viral vectors. However, most of these methods posess some significant drawbacks: they are either too inefficient, or too toxic, or too complicated and tedious to be effectively adapted to biological and therapeutical protocols both in vitro and in vivo. For instance, the most frequently used in vitro calcium phosphate precipitation method is too inefficient (average transfection frequency of 1 in $10^4$ cells). Electroporation is much more efficient than the calcium phosphate method. However, this method is too aggressive (maximum efficiency is obtained at about 50% of cell death) and, in addition, this method requires a special apparatus. Microinjection is efficient, but it is too tedious and not practical. All these methods cannot be used in vivo.

A receptor mediated endocytosis method involves polylysine as a basic polymer for interacting and packaging of DNA. Polylysine has been modified with different ligands (transferrin, insulin, asialoorosomukoid, or galactose) in order to target modified protein-DNA complexes to cell surface receptors: Wu, G. Y. et al. in: J. Biol. Chem. (1987) 262:4429–4432, Cotten, M. et al. in: Proc. Natl. Acad. Sci. (USA) (1990) 87:4033–4037, Huckett, B. et al. in: Biochem. Pharmacol. (1990) 40:253–263, Plank, C. et al. in: Bioconjugate Chem. (1992), 533–539. The method has been dramatically improved by use of inactivated adenovirus to facilitate exit of DNA from endosomes, see: Wagner, E. et al. in: Proc. Natl. Acad. Sci. (USA) (1992) 89:6099–6103, Christiano, R. J. et al. in: Proc. Natl. Acad. Sci. (USA) (1993) 90:2122–2126. The major disadvantage of the described approach includes an inherent inability to control the protein conjugation chemistry and to prepare such conjugates in a reproducible fashion.

At present the best transfection efficiencies both in vitro and in vivo are obtained with retrovirus, adenovirus, and some others, see for example: Kerr, W. G. and Mule, J. J. in: J. Leucocyte Biol. (1994) 56:210–214, Hwu, P. and Rosenberg, S. A. in: Cancer Detect. Prevent. (1994) 18:43–50, Rosenfeld, M. A. et al. in: Cell (1992) 68:143–155. Nevertheless, the use of viral vectors poses several considerations including the requirement of extensive cell culture manipulations, low titers for certain virus systems and the cell tropism of the virus. In addition, immune reactivity against viral vectors may cause problems. Most importantly, the safety issues related to the use of viral vectors are not completely resolved to date.

Liposomes have also been used to introduce DNA into cells both in vitro and in vivo. The most successful liposome systems use different cationic lipids like dioleyloxypropyl-trimethylammonium (DOTMA, which forms a reagent in combination with phosphatidylethanolamine (PE)), dioleoyloxypropyl-trimethylammoniummethyl sulfate (DOTAP), dimethylaminoethane-carbamoyl cholesterol, dioctadecylamidoglycylspermine, 2,3-dioleyloxy-N-(2 (sperminecarboxamido)ethyl)-N,N-dimethyl-1 propanamine (DOSPA), which in combination with PE forms a reagent, see: Felgner, P. L. in: Proc. Natl. Acad. Sci. (USA) (1987) 84:7413–7417, U.S. Pat. No. 5,208,036, Leventis, R. and Silvius, J. R. in: Biochimica et Biophysica Acta (1990), 124–132, Gao, X. and Huang, L. in: Biochem. Biophys. Res. Commun. (1991) 179:280–285, Behr, J.-P. et al. in: Proc. Natl. Acad. Sci. (USA) (1989) 86:6982–6986.

The advantage of using the above mentioned compounds is that the cationic liposome is simply mixed with DNA and added to the cell. Transfection efficiency is usually high when compared to other physical methods of DNA transfer. Besides for delivery of DNA, a specific compound has been used to deliver mRNA and proteins into cultured cells, see: Malone, R. et al. in: Proc. Natl. Acad. Sci. (USA) (1989) 86:6077–6081, and Debs, R. et al. in: J. Biol. Chem. (1990) 265, 10189–10193. Some of the above mentioned compounds have been used to transfect reporter or therapeutically utile genes in vivo, see: Nabel, G. J. et al. in: Proc. Natl. Acad. Sci. (USA) (1993) 90:11307–11311, Zhu, N. et al. in: Science (1993) 261:209–211. Finally, a DNA transfection protocol has been developed that makes use of the cyclic cationic peptide gramicidin S and PE, see: Legendre, J.-Y. and Szoka, F. C. in: Proc. Natl. Acad. Sci. (USA) (1993), 90:893–897. The above mentioned system takes advantage of the DNA binding ability and the membrane destabilization properties of gramicidin S.

The main disadvantage of cationic liposomes includes their relatively high cytotoxicity. In addition, most of the above mentioned compounds are not active or show highly reduced activity in the presence of serum. Most of them need the use of PE, possibly because PE can form intramembrane lipid intermediates which facilitate membrane fusion. Studies on the mechanism responsible for transfection using the cationic lipids have not been fully addressed to date. The need exists, therefore, for a less toxic, non-infectious and more efficient delivery of biological molecules into the cytoplasm and nuclei of living cells.

The object of the present invention is to overcome the above mentioned and other drawbacks of the state of the art. According to a first aspect there are lipid compounds to be provided to allow an improvement of the transport of biologically active agents or molecules through membranes and thus in cells or cell organelles.

This object is solved primarily by the compounds according to claim 1. Preferred compounds are claimed in the subclaims 2 to 11. Derivated products and applications of the novel compounds according to the invention are mentioned in claims 12 to 24 (complexes), claims 25 and 26 (methods for the preparation of complexes), claim 27 (liposome), claims 28 to 32 (liposome formulations) and claims 33 to 42 (methods for the transport of substances and agents through membranes). The wording of all the claims is included into the description by reference.

The compounds according to the invention are illustrated by formula I as follows:

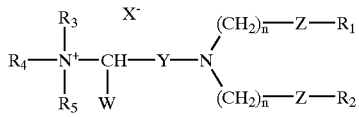

I wherein
- $R_1$ and $R_2$ are the same or different and are an alkyl, alkenyl, or alkynyl group of 6 to 24 carbon atoms;
- $R_3$, $R_4$, and $R_5$ are the same or different and are hydrogen, alkyl, or alkylamine, having from 1 to 8 carbon atoms, or an amino acid, an amino acid derivative, a peptide, or a peptide derivative;
- W is hydrogen, a carboxyl group, or a side chain group of amino acids, amino acid derivatives, peptides or peptide derivatives;
- Y is a linking group having at least one atom other than hydrogen, particularly —CO—, —$(CH_2)_m$CO—, —$(CH_2—)_m$, —$(CHOHCH_2—)_m$, wherein m is from 1 to 20, —$CH_2$—S—$CH_2$—, —$CH_2$—SO—$CH_2$—, —$CH_2$—$SO_2$—$CH_2$—, —$CH_2$—$SO_2$— or —$SO_2$—;
- Z is an ester, ether or amide bond;
- n is from 1 to 8; and
- X is an anion, particularly a pharmaceutically acceptable anion.

The compounds according to the invention comprise lipids (detergents, surfactants) the main characteristics of which are well-known. The compounds comprised by formula I can be present in the form of their optical isomers (R- or S-configuration) or in the form of mixtures thereof.

According to formula I the lipid compounds are prepared in the form of ionic salts. This is due to the fact that per se neutral compounds are present as ions in (aqueous) solution. Of course the invention is also to include the corresponding neutral compounds. The compounds according to formula I can be provided with further charges by appropriate selection of substituents, for example in the substituent W by appropriate selection of the side chain group of an amino acid.

For a better understanding of the claims and description are given the following definitions:

- Alkyl refers to a fully saturated branched or unbranched carbon chain radical.
- Alkenyl refers to a branched or unbranched unsaturated carbon chain radical having one or more double bonds.
- Alkynyl refers to a branched or unbranched unsaturated carbon chain radical having one or more triple bonds.
- Amino acids refer to a monomeric unit of a peptide, polypeptide or protein. The twenty protein amino acids (L-isomers) are: alanine ("AA"), arginine ("R"), asparagine ("N"), aspartic acid ("D"), cysteine ("C"), glutamine ("Q"), glutamic acid ("E"), glycine ("G"), histidine ("H"), isoleucine ("I"), leucine ("L"), lysine ("K"), methionine ("M"), phenylalanine ("F"), proline ("P"), serine ("S"), threonine ("T"), tryptophane ("W"), tyrosine ("Y"), and valine ("V"). The term amino acid, as used herein, also includes analogues of the protein amino acids, D-isomers of the protein amino acids, β-, y- and other amino acids, unnatural amino acids, and their analogues.

Biologically active substance refers to any molecule or mixture or complex of molecules that exerts biological effect in vitro and/or in vivo, including pharmaceuticals, drugs, proteins, steroids, vitamins, polyanions, nucleosides, nucleotides, polynucleotides, etc.

Buffers referred to in this disclosure include: "Hepes" which is N-2-hydroxyethylpiperazine-N'-2-ethanesulfonic acid and used here as a buffer at about pH 7; "PBS" is a phosphate buffer saline, and is 10 mM phosphate and 0.9% wt. NaCl, used here as an isotonic physiological buffer at pH 7.4; "Transfection buffer" is 10 mM Hepes and 0.9% wt. NaCl and used here as a buffer at about pH 7.4; "Tris" is tris(hydroxymethyl)amino methane, also used here as a buffer at about pH 7.

Cell-targeted complexes or liposomes applied to the cells include further molecules, e. g. on their surfaces, capable of recognizing a component on the surface of said targeted cell. Cell recognition components include: ligands for cell surface receptors, antibodies to cell surface antigens etc.

Charge-masked complexes or liposomes are to be understood as positively charged, comprising a compound of formula I and a bound polymer which covers the surface of the liposome, for example. A polymer can be covalently linked to any lipid forming the liposome, or be adsorbed on their surface.

A complex is defined as the product made by mixing of two or more components. Such a complex is characterized by a non-covalent interaction (ionic, hydrophilic, hydrophobic etc.) between two or more components.

DNA represents deoxyribonucleic acid which may comprise unnatural nucleotides. DNA may be single-stranded or double-stranded.

Drug refers to any prophylactic or therapeutic compound which is used in the prevention, diagnosis, alleviation, treatment, or cure of disease in a human or an animal.

A liposome formulation is a composition of substances including a liposome which includes entrapped material for diagnostic, biological, therapeutic or other use.

An optional co-lipid is to be understood as a compound capable of producing a stable liposome, either alone, or in combination with other lipid components. Examples of optional co-lipids are phospholipid-related materials, such as lecithin, phosphatidylcholine, dioleylphosphatidylcholine (DOPC), phosphatidylethanolamine (PE), phosphatidylserine, phosphatidylglycerol, phosphatidylinositol, sphingomyelin, cephalin, cardiolipin, phosphatic acid, cerebrosides, dicetylphosphate, etc., non-phosphorous lipids like steroids and terpenes. Additional non-phosphorous lipids are, e. g. stearylamine, dodecylamine, hexadecylamine, acetylpalmitate, glycerol ricinoleate, hexadecyl stearate, isopropyl myristate, dioctadecylammonium bromide, amphoteric polymers, triethanolamine lauryl sulfate, cationic lipids described before and the like.

A pharmaceutically acceptable ion is an ion which itself is non-toxic.

A polyanion is a polymeric structure, where more than one unit of the polymer bears a negative charge and the net charge of the polymer is negative.

A polycation is a polymeric structure, where more than one unit of the polymer bears a positive charge and the net charge of the polymer is positive.

A polynucleotide is DNA or RNA containing more than one nucleotide. Polynucleotides are intended to include cyclic polynucleotides and unnatural nucleotides, and can be made by chemical methods, or by use of recombinant technology, or by both.

A polypeptide is to be understood as a series of two or more amino acids coupled via covalent linkage.

RNA represents ribonucleic acid which may comprise unnatural nucleotides. RNA may be single-stranded or double-stranded.

Preferably the above described compounds according to formula I comprise Y that is carbonyl, i. e. —CO—. This results in a linkage of the peptide bonding type —CO—N<.

With the lipid compounds according to formula I the group Z preferably includes an ester linkage, i. e. the group —O—CO—.

In further preferred embodiments $R_1$ and $R_2$ include an alkyl or alkenyl group of 10 to 20 carbon atoms, preferably 12 to 18 carbon atoms. The groups $R_1$ and $R_2$ are preferably the same. Of the described preferred groups the alkenyl groups are preferred. Accordingly, the groups $R_1$ and $R_2$ comprise, besides palmityl or stearyl groups, preferably the oleyl group or moieties of the linolic or linoleic acid.

In formula I preferably n is 2. Further, the group W preferably is a side chain group of a basic amino acid, in particular a side chain group of lysine or ornithine.

The groups $R_3$, $R_4$ and $R_5$ may be alkyl groups having 1 to 8 carbon atoms, in particular the methyl group. Preferably the three groups $R_3$, $R_4$ and $R_5$ are the same. In a particularly preferred embodiment $R_3$, $R_4$ and $R_5$ are hydrogen.

Generally, all conceivable anions may be used as counterion X, with pharmaceutically acceptable anions being preferred for most applications of the present invention. Preferably X may be a halide anion, in particular a chloride anion.

Preferred compounds according to formula I are given in claim 10, to which particular reference is made. A particularly preferred compound is L-lysine-bis-(O,O'-cis-9-octadecenoyl-β-hydroxyethyl)amide-dihydrochloride or an optical isomer thereof.

Compounds covered by the definition of formula I and preferred according to the invention can be prepared by preparing the corresponding compound using the following coupling:

amino acid or peptide-----dialkanol amine-----fatty acid or fatty alcohol

Compounds preparable in this manner are particularly adapted to the applications which will be discussed below. Said compounds are characterized in particular by a considerably minor toxicity than so far known lipid compounds used for similar applications.

Besides the described lipid compounds the invention includes complexes which will be prepared by means of said novel compound. The expression "complex" is to be understood in the sense of the above definition. It is not necessarily a completely formed liposome. However, as the exact mechanisms of the complex formation are not known, the case that primarily liposomes are formed from lipides and these in turn will complex with polyanions, polycations or complexes thereof, is not excluded according to the invention.

The characteristics of the complexes according to the invention are claimed and described in claims 12 to 17, and 18 to 24, respectively. Explicit reference is made to these claims. The complex formation relies essentially on the fact that the compounds according to the invention have a positive charge.

The ratio between lipide compound and the other constituents of the complex, that is in the (binary) polyanion-lipid complexes the ratio polyanion and lipid compound, may be varied considerably upon the desired application. Preferably, in favour of the lipid compound this ratio is larger than 1:1 (considering charge), so that a positive total or netto charge is resulting for the complex to allow an interaction with the negatively charged surface of biological membranes in a simple manner. If necessary a particularly advantageous ratio will be determined experimentally. Thus for example, in a DNA transfection that ratio of DNA and lipid compound will be determined by experiment which results in an optimized expression of the transfected DNA.

Generally the complexes according to the invention can be realized with all molecules having a negative charge. Preferred are such complexes that use a polynucleotide as the polyanion.

In the ternary complexes given in claims 18 to 24 it is preferred that the polycation is a polypeptide. Generally it is possible to use neutral polypeptides for the formation of ternary polynucleotide-polypeptide-lipid complexes which are also to be covered by the present invention.

Surprisingly, during the formation of ternary complexes was found, for example, that by using polypeptides, the transfection of polynucleotides will be increased significantly as compared to the use of polynucleotide-lipid complexes. The peptide sequences mentioned in claim 23, to which explicit reference is made, can be used preferably. The first sequence represents the C-terminal portion of the nucleoprotein of the hepatitis B virus (HBV). Although a final scientific explanation is not available at present, there seems to be a possible correlation of the positive effect of these peptide sequences in the ternary complexes and the comparably high portion of basic amino acids in the sequences.

The described complexes for particular applications can optionally be charge-masked or cell-targeted for interaction with particular cells or cell organelles.

Further the invention comprises the methods of claims 25 and 26 for the preparation of the complexes according to the invention. The preparation and the contacting involved therein are realized by common methods as well-known to those skilled in the art. Thus for example, in the preparation of binary complexes are combined buffer solutions including the polyanion and the lipid compound, respectively. In a corresponding manner is the preparation of ternary complexes, wherein first a polyanion-polycation complex is obtained in a buffer solution and subsequently the buffer solution is combined with a buffer solution containing the lipid compound.

Further the invention comprises liposomes, which are preparable or prepared from at least one of the lipid compounds according to the invention. The preparation of the liposomes is performed in conventional ways well-known in the state of the art.

Further the invention comprises liposome formulations in aqueous solution including at least one biologically active substance (material, molecule etc.) and one lipid component. Therein the lipid component comprises at least one of the lipid compounds according to the invention. Besides the biologically active substance and the lipid component the liposome formulation includes conventional solution constituents of an aqueous solution, which may be a solution in pure water or preferably conventional buffer solutions.

As is given in the wording of claim 28, a single compound of formula I or a mixture of such compounds may be applied as a lipid component. Furthermore it is possible, to use the compound or compounds according to the invention with additional co-lipids as defined above, for example PE, POPE in mixture.

As long as liposome formation is possible, the amount of biologically active substance is generally not critical. Commonly the substance will be present in amount of up to 10% by weight in the liposome formulation. A value of, for example, 0.01% by weight is to be mentioned as a lower limit. A concentration range of 1 to 5% by weight of biologically active substance is preferred.

The compound according to the invention can preferably amount to 1% to 100% of the lipid component. In preferred embodiments of the liposome formulation there will be one or more co-lipids present, wherein such co-lipids amount to 30 to 70% of the lipid component.

In case the biologically active substance is a drug, the amount thereof is conventionally selected according to the desired therapy. Preferably there will be 1 to 5% by weight of the drug present in the liposome formulation. In case of drugs applied as biologically active substance, there can pharmaceutically acceptable excipients be present in the liposome formulation.

As mentioned above with the complexes according to the invention, also the liposomes or liposome formulations according to the invention will optionally be charge-masked or cell-targeted for interaction with certain cells.

Finally, the invention comprises methods for the transfer of polyanions or polycations or for the transfer of biologically active substances in general through biological membranes, in particular for introduction in cells or cell organelles. In this context particular reference is made to claims 33 to 38, and 39 to 42, respectively. For the methods according to the invention can be used either the compounds according to the invention themselves or compositions including such compounds.

During the performance of the method by incubation in vivo there can additional stabilizers be present, like for example polyethylene glycol.

Further details of the method according to the invention will be described below.

The compounds and other parts of the present invention have various advantages. One of the advantages of the compounds described here are that they allow up to 100% inclusion of polyanionic materials in a convenient protocol. On the other hand, the incubation of positively charged complexes with negatively charged cell surfaces results in a rapid and improved uptake, in particular of polyanionic substances and other biologically active compounds in general. The latter allows the introduction of complexed or included polyanionic substances like for example DNA, in an amount not known so far with such cells.

The particular advantages of the compounds disclosed herein are as follows. First, these compounds represent the novel liposome forming lipids. The geometry of both the aliphatic chains in the compounds of formula I allows their organization in stable double layer structures. The polar head (e. g. amino acid) can be varied as a function of the application. This will allow the easy introduction of different modifications to the amino group, the side chain or the bonding, for example. The cytotoxicity of most of the cationic compounds disclosed here are favourable as compared to that reported with other cationic amphiphiles. All the bondings illustrated in formula I will readily be hydrolized in the cells which results in the formation of non-toxic compounds.

Further, the positively charged lipids of formula I have an improved transfection efficiency in the presence of serum, in contrast to other cationic lipids of the state of the art. The ability to transfect cells in the constant presence of serum is advantageous for various reasons: transfection occurs more easily and is less time consuming, the requirements as to media and serum are reduced, the cells are not depleted of serum which could deteriorate cell functions and viability.

The second specific advantage over the disclosed state of the art is derived from the novel method for the introduction of polynucleotide (in particular DNA) into ternary complexes. Said complex is in particular formed from positively charged lipids of formula I and a complex made of polynucleotide and cationic polypeptide. According to the method there will be formed a first complex made of polynucleotide-cationic polypeptide which in the following step will be complexed with a positively charged lipid of formula I. An exact regulation of the composition will determine the biological activity of the final complex.

The advantage of this procedure in relation to the transfection steps known in the state of the art is for example the fact that the novel method results in an up to 300 times increased transfection efficiency. Furthermore, by using the novel method, a detection of transfection (e. g. detection of the expressed protein) will easily be registered after less than two hours from the start of transfection. Further, the novel procedure allows working in "microscale" for cell transfection (for example 96-well size) which is desirable for the screening of a large number of samples and allows automation of the process in total.

The compounds of formula I are particularly useful in the preparation of liposomes, however, they can be used in other cases where cationic lipids find application. They may be used in industrial applications, for example. Of particular interest is the application of said compounds in combination with cationic lipids which are acceptable for pharmaceutical formulations (creams, pastes, gels, colloidal dispersions and the like) and/or cosmetic compositions (makeups, lipsticks, polishes, body lotions, moisturizing creams, shampoos and the like).

Formulations comprising the compounds of formula I are advantageous for achieving desirable intracellular delivery of biologically active substances, such as polynucleotides, peptides, proteins, steroids and other natural or synthetic compounds. The intracellular delivery can be into the cytoplasm, into the nucleus, or both. Such intracellular delivery can be achieved in tissue culture (in vitro) and may be used, for example, for transfecting cells with desired polynucleotides (e. g. DNA), or delivery of proteins and the like.

Formulations comprising the compounds of formula I can also be used for ex vivo therapy, where cells isolated from the organism are transfected in vitro and then implanted to the organism. An example of this application is to transfect bone marrow cells.

Intracellular delivery can also be achieved in the whole organism (in vivo) and thus may be useful in several applications like gene therapy, antisense and antigene therapy. Intracellular delivery in vivo can also be used for DNA vaccination with an aim to induce immune response (humoral and/or cellular) to the desired protein.

Intracellular delivery utilizing compounds of formula I is also useful for delivery of anticancer and antiviral compounds, antibiotics and the like.

Cell selectivity can be achieved by incorporating cell recognition compounds, for example on the surface of the vesicle such as antibodies, ligands for cell-surface receptors and the like. Increased stability and further selectivity can be achieved by coating the liposome vesicle with an appropriate charge-masked natural or synthetic compound such as polymers and neutral, or negatively charged lipids.

Liposome vesicles comprising compounds of formula I can be used for the induction of a specific immune response to an antigen of interest which is incorporated in the liposome. Additional components, like N-palmitoyl-S-(2,3-bis(palmitoyl-oxy)-(2RS)-propyl)-R-cystein (Pam$_3$Cys) or N-acetyl-myramyl-L-threonyl-D-isoglutamine (MDP) and derivatives thereof, may be particularly useful.

Compounds of formula I are of interest for the introduction of a lipophilic moiety into polymers, and particulary in peptides in order to increase their uptake by a cell, or to increase their incorporation in the lipid-containing vesicles and the like. Activated compounds of formula I can also be used for modification of proteins.

Further details of the so far presented parts of the invention will be apparent from the following description of preparation procedures, lipid compounds and examples for application thereof. In the description of each example reference will be made to the accompanying drawings.

Method for the Preparation of Selected Compounds of Formula I

Using well-known techniques, a person skilled in the art can readily make additions, deletions or substitutions, increase or decrease the preferred polypeptide amino acid sequences, or simply use another sequence encoding for different cationic polypeptides. It should be understood, however, that such variations are within the scope of this invention. It should also be understood that the examples provided below are for illustrative purposes only and are not to be construed as limiting this invention in any way.

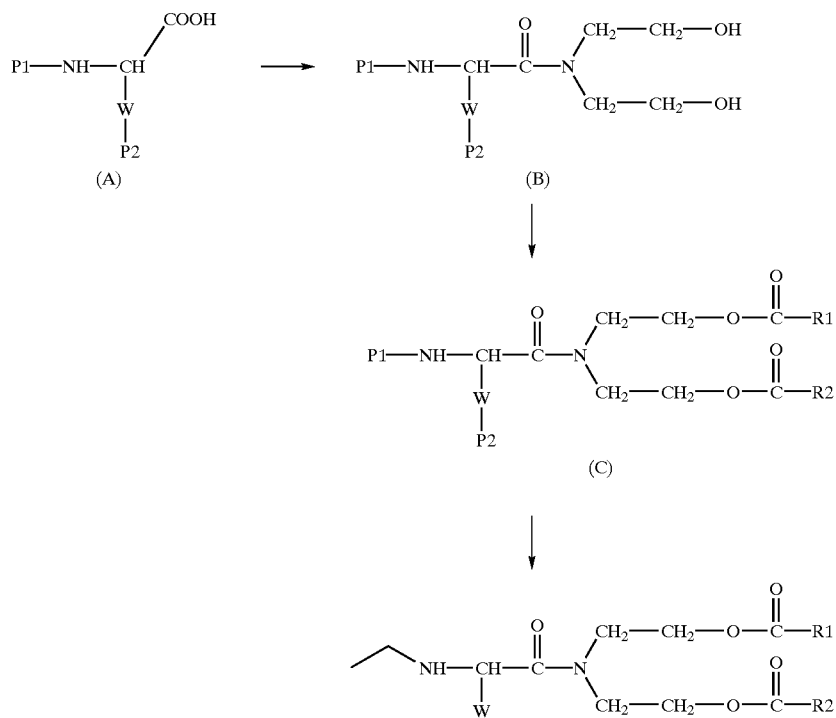

This reaction scheme is applicable to the sythesis of preferred compounds of formula I, wherein Z is an ester bond and n is 2. In this reaction scheme $P^1$ and $P^2$ are protecting groups, and are the same or different; W is a side chain of amino acid, $R^1$ and $R^2$ are the same and are alkyl or alkenyl having 6 to 24 carbon atoms.

Compounds of formula (A) are commercially available in the optically pure form. To effect the formation of compounds of formula (B), the carboxyl group of the amino acid of formula (A) is activated with an appropriate agent, and is then allowed to react with the imino group of diethanol amine. Methods for activation of amino acids are known in the art. For example, dicyclohexylcarbodiimide/N-hydroxysuccinimide method can be used for epimerization-free amidation of protected amino acids.

The amide of formula (B) is prepared by dissolving the amino acid of formula (A) and a preformed salt of N-hydroxysuccinimide and diethanolamine in an appropriate polar solvent such as dimethylformamide. The mixture is cooled to 0° C. and then a solution of dicyclohexylcarbodiimide is added. This reaction is effected by stirring the solution for one hour at 0° C. and eight hours at room temperature. The resulting amide of formula (B) is then recovered by some standard separatory means.

To effect the formation of compounds of formula (C), the amide of formula (B) is dissolved in an appropriate solvent (e. g. dichloromethane). To this is added an appropriate tertiary amine, such as, for example, triethylamine in an excess molar amount. The mixture is cooled to about 0° C. The alkylating agent of the desired chain length and degree of unsaturation is added in an excess molar amount, preferably about 3 to about 4 times the amount of the amide of formula (B). For example, oleoylchloride can be used to effect the addition of 9-octadecenoyl groups. This mixture is then stirred for approximately 3 hours under $N_2$ atmosphere at room temperature. The product of formula (C) is then extracted. The compound of formula (C) is then deprotected in an appropriate way, depending on the used protecting groups, extracted and further purified by chromatographic means.

EXAMPLE 1

Synthesis of L-Lysine-bis(O,O'-oleoyl-β-hydroxyethyl)amide dihydrochloride (1)

Boc-Lys(Boc)-OH *DCHA (2.63 g, 5 mmol) was suspended in ethylacetate and converted to the free acid using ice cold 2 M $H_2SO_4$. Boc-Lys(Boc)-OH in ethylacetate was dried with $MgSO_4$ and evaporated to dryness. The residual oil was dissolved in about 15 ml of dimethylformamide (DMF) containing 1.1 g (5 mmol) of a preformed salt of N-hydroxysuccinimide and diethanolamide (HOSu*N (EtOH)$_2$) and was cooled at 0° C. with ice-water. While stirring, a solution of 1.13 g (5.5 mmol) of dicyclohexyl-carbodiimide (DCC) in 5 ml of DMF was added to the mixture which was stirred for one hour at 0° C. and then continuously at room temperature for another 8 hours. The mixture was concentrated to dryness in vacuum. After the addition of about 50 ml of ethylacetate to the residue, most of the dicyclohexylurea (DCU) precipitated and was filtered off. The ethylacetate phase was washed with aqueous solutions of $NaHCO_3$ (5%) and citric acid (5%) in 0.1 M of NaCl, dried with $MgSO_4$ and evaporated to dryness to give 1.7 g of the crude product as a colorless oil.

A solution of 1.7 g (3.92 mmol) of Boc-Lys(Boc)-N(EtOH)$_2$, 1.64 ml of triethylamine and 3.93 mol of oleoyl-chloride (11.7 mmol each) in 50 ml of dichloromethane (DCM) was stirred for 30 min at 0° C. and 4 hours under $N_2$ atmosphere in the dark at room temperature. The mixture was quenched with methanol, concentrated in vacuum, redissolved in hexane and washed three times with 0.1 M KOH in methanol/water (1:1 vol.) at 0° C., then once with 0.1 M aqueous NaCl. The hexane phase was concentrated in vacuum and the residual was treated with 50 ml of a mixture of trifluoroacetic acid (TFA)/DCM (1:1 vol.) for 40 min at room temperature. The mixture was repeatedly mixed with toluene and reconcentrated in vacuum, and then applied in chloroform to a column of Silica Gel 60. The column was eluted with an ascending gradient of methanol in chloroform, and the pure compound (2.3 g, 62% yield) eluted at about 20% methanol. The hydrochloride was prepared by dissolving the product in dry ethylacetate saturated with HCl gas and evaporating to dryness. (Analysis: ES-MS: Mol. mass determined=762 (calculated=762); TLC: Rf=0.69 in ethylacetate:acetic acid:water=(4:1:1); HPLC: Rt=14.19 min; column Nucleosil C2 4.0×100 mm, gradient 30 to 90% of acetonitrile in 0.1% of TFA in water within 20 min).

In a similar manner, but substituting the appropriate starting material, the following compounds were prepared:

L-Lysine-bis-(O,O'-palmitoyl-β-hydroxyethyl)amide dihydrochloride (2)
L-Lysine-bis-(O,O'-myristoyl-β-hydroxyethyl)amide dihydrochloride (3)
L-Ornithine-bis-(O,O'-myristoyl-β-hydroxyethyl)amide dihydrochloride (4)
L-Ornithine-bis-(O,O'-oleoyl-β-hydroxyethyl)amide dihydrochloride (5)
L-Ornithine-bis-(O,O'-palmitoyl-β-hydroxyethyl)amide dihydrochloride (6)
L-Arginine-bis-(O,O'-oleoyl-β-hydroxyethyl)amide dihydrochloride (7)
L-Arginine-bis-(O,O'-palmitoyl-β-hydroxyethyl)amide dihydrochloride (8)
L-Serine-bis-(O,O'-oleoyl-β-hydroxyethyl)amide dihydrochloride (9)
Glycine-bis-(O,O'-palmitoyl-β-hydroxyethyl)amide dihydrochloride (10)
Sarcosine-bis-(O,O'-palmitoyl-β-hydroxyethyl)amide dihydrochloride (11)
L-Histidine-bis-(O,O'-palmitoyl-β-hydroxyethyl)amide dihydrochloride (12)
L-Glutamine-bis-(O,O'-palmitoyl-β-hydroxyethyl)amide dihydrochloride (13)

EXAMPLE 2

Synthesis of N-α-tert-butoxycarbonyl-L-aspartic acid-α-N'-bis (O,O'-palmitoyl-β-hydroxyethyl) amide (Boc-Asp-N(EtOPalm)$_2$ (14) and N-α-fluorenylmethyloxycarbony-L-aspartic acid-α-N'-bis-(O,O'-palmitoyl-β-hydroxyethyl)amide (Fmoc-Asp-N(EtOPalm)$_2$ (15)

The compound Boc-Asp(OBzl)-N(EtOH)$_2$ was prepared in the same manner as described above for preparing compound Boc-Lys (Boc)-N(EtOH)$_2$. The compound Boc-Asp (OBzl)-N(EtOPalm)$_2$ was prepared similar to the compound Boc-Lys(Boc)-N(EtOOL)$_2$ with minor modifications. The reaction proceeded overnight, the mixture was diluted with ethylacetate and then poured into a saturated aqueous solution of $NaHCO_3$ to destroy residual palmitoylchloride and precipitate sodium palmitate. The precipitate was filtered off and the organic phase was evaporated to dryness and redissolved in hot methanol. The product was precipitated in cold methanol and collected by filtration with the yield of 55% (TLC: Rf=0.64 in chloroform:methanol=100:2). The benzyl-protecting group was removed from the product (1.5 g) by treating it overnight with $NH_4COOH$ (0.65 g) in the presence of freshly prepared Pd black (about 0.1 g) in 15 ml of DMF. Pd black was filtered off and the mixture was evaporated in vacuo. The residual was precipitated from methanol/water solution to give the desired product Boc-Asp-N (EtOPalm)$_2$ (14) with the yield of 85%. (Analysis: ES-MS: Mol. mass determined=796,5 (calculated=796); TLC: Rf=0.4 in chloroform:ethyl acetate:methanol=9:3:1).

0.5 g (0.62 mmol) of Boc-Asp-N(EtOPalm)$_2$ was treated with a mixture TFA/DCM=1:1 for 30 min at room temperature. The mixture was repeatedly evaporated with toluene. The residual was dissolved in 10 ml of DMF, neutralized with diisopropylethylamine (DIPEA) and was reacted for two hours with 1.2 equivalents of 9-fluorenylmethyl-succinimidyl-carbonate (Fmoc-OSu). The reaction mixture was evaporated and redissolved in methanol. The desired compound Fmoc-Asp-N(EtOPalm)$_2$ (15) was precipitated to afford 0.44 g of the compound with a yield of 77%. (Analysis: TLC: Rf=0.4 in chloroform:ethyl acetate:methanol=9:3:1).

Using similar procedures, but substituting the appropriate starting material, the following compounds were prepared:

N-α-tert-butoxycarbonyl-L-glutamic acid-γ-N'-bis-(O,O'-palmitoyl-β-hydroxyethyl)amide Boc-Glu(N(EtOPalm)$_2$)-OH (16)

N-α-fluorenylmethyloxycarbonyl-L-glutamic acid-γ-N'-bis-(O,O'-palmitoyl-β-hydroxyethyl)amide Fmoc-Glu(N(EtOPalm)$_2$)-OH (17)

N-α-tert-butoxycarbonyl-L-aspartic acid-β-N'-bis-(O,O'-palmitoyl-β-hydroxyethyl)amide Boc-Asp(N(EtOPalm)$_2$)-OH (18)

In addition, intermediates of their synthesis, or of the above described synthesis, can be used for the preparation of liposomes:

L-glutamic acid-γ-N'-bis-(O,O'-palmitoyl-β-hydroxyethyl) amide H-Glu(N(EtOPalm)$_2$)-OH (19)

L-aspartic acid-β-N'-bis-(O,O'-palmitoyl-β-hydroxyethyl) amide H-Asp(N(EtOPalm)$_2$)-OH (20)

L-aspartic acid-α-N'-bis-(O,O'-palmitoyl-β-hydroxyethyl) amide H-Asp(N(EtOPalm)$_2$) (21)

Preparation and Characteristics of a Complex Made of DNA and Compound (1)

EXAMPLE 3

Fluorescence studies. Fluorescence measurements were carried out on an Aminco SPF-1000Sc spectrophotometer, using a 1 cm light path cell with a slit width for excitation and emission of 10 nm. The binding of (1) to nucleic acids was observed from the displacement of ethidium bromide, which upon intercalation in between the DNA base pairs acts as a fluorescence probe. Fluorescence was measured immediately following addition of increasing amounts of (1) to DNA complexed with ethidium bromide (5 μg/ml calf thymus DNA, $8 \times 10^{-6}$ M bp (base pairs); ethidium bromide 1:50 bp in 10 mM Hepes, 150 mM NaCl, pH 7.4). Ethidium bromide displacement was monitored by the decrease of the ethidium bromide fluorescence (excitation=540 nm, emission=600 nm) that occurs when it is released from DNA (FIG. 1). Fluorescence intensity is gradually decreased with increasing concentration of the cationic lipid. This is an indication for compaction and/or aggregation occurring in DNA. The ratio between (1) and DNA at which the fluorescence quenching does not change any more, corresponds to about 6:1 (w/w). The obtained ratio corresponds to the charge ratio of about 3.5:1.

Transfection of Cells

EXAMPLE 4

Cell cultures and plasmids

HeLa (CCL2, epitheloid carcinoma, human), COS-7 (CRL 1651, kidney, SV-40 transformed, African green monkey), HT-29 (HTB 38, adenocarcinoma, colon, human), CV-1 (CCL 70, kidney, African green monkey), 818-4 (adenocarcinoma, pancreas, human), H4IIE (CRL 1548; hepatoma, rat), K562 (CCL 243; chronic myelogenous leukemia, human), HL-60 (CCL 240; promyelotic leukemia, human) were grown in 5% CO$_2$ at 37° C. on plastic tissue culture flasks in RPMI 1640 or DMEM with 10% fetal calf serum and supplemented with penicillin at 100 units per ml, streptomycin at 100 μg per ml, 2 mM glutamine and 0.1 μM dexamethasone for H4IIE cells.

Plasmids pCMVL and pCMVμ-gal encode luciferase and β-galactosidase genes, respectively, and their expression is under control of the cytomegalovirus (CMV) immediate-early promoter. Plasmids pZeoSV and pZeoSVLacZ encode the Sh-ble resistant protein to Zeocin™ (registered trademark) which allows for selection both in prokaryotic and eukaryotic cells. Eukaryotic expression is under control of the CMV promoter. pZeoSVLacZ in addition encodes β-galactosidase gene under control of the SV40 early enhancer-promoter. Plasmid DNAs were purified on a QIAGEN™ (registered trademark) column using the QIAGEN™ plasmid purification procedure.

Transfection of tissue culture cells. Preparation of cells, transfection protocol and assays for transfection efficiency. The details of the individual transfections are given in the result section.

a) Adherent Cells

At about 24 hours before transfection nearly confluent cell monolayers were trypsinized. The cells were resuspended in fresh medium and placed either in 24-well plates ($5 \times 10^4$ cells per well) or in 6-well plates ($2-2.5 \times 10^4$ cells per well). Just before transfection, the cells were placed in fresh medium with or without 10% FCS. In general, cells were transfected at 50 to 70% confluence. 24 hours after transfection, cells were washed three times with 2 ml of PBS and lysed in 100 μl (24-well plates) or 200 μl (6-well plates) of lysis buffer (77 mM K$_2$HPO$_4$, 23 mM KH$_2$PO$_4$, 0.2% Triton X-100, 1 mM dithiotreitol, pH 7.8). Cell debris was removed by centrifugation (14000 rpm for 2 min). Usually, enzyme activity (see below) was determined directly after cell lysis. However, lysates can be stored at −20° C. without loss of activity.

b) Suspension Cells

At 24 hours before transfection, the cells were placed in fresh complete growth medium. Just before transfection, the cells were collected, resuspended in fresh medium with or without 10% FCS at $0.25 \times 10^6$ cells per ml, and placed in 24-well plates, 2 ml per well.

The cells were normally harvested 24 hours after transfection (the time of harvesting is an important variable and should be optimized), collected by centrifugation and resuspended in 10 ml of PBS, again centrifuged, and the cell pellet was transferred into a 1.5 ml Eppendorf tube with 1 ml PBS. The cells were centrifuged in the Eppendorf centrifuge (14000 rpm for 20 sec), The resulting cells were lysed in 100 μl of lysis buffer (described above). The sample was then centrifuged (14000 rpm for 2 min) and the supernatant was carefully transfered to a fresh centrifuge tube.

c) Transfection Protocols

Transfection of cells using compound (1). Plasmid DNA (from a stock solution of a concentration of about 1 mg/ml) and cationic lipids (from a stock solution of a concentration 1 to 2 mg/ml) were diluted separately in 1.5 ml Eppendorf tubes with 10 mM Hepes, 0.9% NaCl buffer, pH 7.4, to the final volume of 100 μl. The amount of DNA in typical transfections varied from 1 to 2 μg per 100 μl. The amount of a cationic lipid varied from 0 to 20 μg per 100 μl. Two solutions were mixed together to form a DNA-lipid solution. After incubation for 10 min at room temperature the resultant DNA-lipid solution was added to the cell cultures, growing as described before, and gently mixed. Alternatively, the DNA-lipid solution was diluted with 800 μl (for 24- or 6-well plates) of the appropriate medium (+/−FCS) and mixed. The diluted solution was then overlayed onto the cells, rinsed with the appropriate medium. The complexes were incubated with the cells for 1 to 24 hours. A typical incubation time in the absence of serum was 4 hours. The transfection medium was then substituted with a complete growth medium. In the presence of serum, the transfection medium was usually not replaced and the cells continued to grow in the presence of complexes until the end of experiments (one step transfection). After 24 hours cells were worked up as described above.

Transfection of cells using ternary complexes of (1) Plasmid DNA was diluted with 10 mM Hepes, 0.9% NaCl buffer (pH 7.4) containing the appropriate peptide (for example according to claim 23) to the final volume of 100 μl. The amount of a peptide varied between 0 to 20 μg per 100 μl of buffer. A typical concentration was 2 to 5 μg peptide per 100 μl of buffer. After incubation for 10 min, the resultant solution was mixed with 100 μl of a cationic lipid solution, and the whole procedure was continued as described above.

d) Enzyme Assays

Luciferase assay. The luciferase activity in cell extracts was assayed using a Berthold Lumat instrument (LB 9501). The luciferase assay was performed by adding 5 to 10 μl of cell extract. The sample was placed in the LB 9501 and the instrument automatically injected 100μl of the injection buffer (20 mM tricine, 1.07 mM $(MgCO_3)_4Mg(OH)_2$, 2.67 mM $MgSO_4$, 0.1 mM EDTA, 33.3 mM DTT, 270 μM coenzyme A, 470 μM luciferin, 530 μM ATP, pH 7.8) into the sample, measured light emission and displayed it as an integrated value for the first 10 sec of light production.

β-Galactosidase assay. β-Galactosidase activity in cell extracts was measured on the 96-well microtiter plates. 10 μl of cell extracts were diluted with 70 μl of "β-Gal" buffer (33 mM $NaH_2PO_4$, 66 MM $Na_2HPO_4$, 2 mM $MgSO_4$, 40 mM β-mercaptoethanol) and 25 μl of ONPG solution (o-nitrophenyl-β-D-galactopyranoside 4 mg/ml in B-Gal buffer). The mixture was kept at 37° C. for 30 min to 1 hour and the reaction was stopped by adding 150 μl of 1 M sodium bicarbonate. The absorbance was measured at 405 nm.

Staining of cells with 5-bromo-4-chloro-3-indolyl-β-D-galactopyranoside (X-Gal). The rinsed cells were fixed with 1% glutaraldehyde solution in 0.1 M sodium phosphate, 1 mM $MgCl_2$ buffer (pH 7.0) for 15 min at room temperature. The fixing solution was removed, cells were washed three times with PBS, and staining solution (0.2% X-Gal, 10 mM sodium phosphate, 150 mM NaCl, 1 MM $MgCl_2$, 3.3 MM $K_4Fe(CN)_6$ and 3.3 mM $K_3Fe(CN)_6$, pH 7.0) was overlayed onto the cells and incubated for 1 to 8 h at 37° C. The stained cells on culture dishes or cover slides were visualized using inverted or phase contrast microscopes, respectively.

Protein determination. Protein content in the supernatant was assayed using the technique of Lowry (Bio-Rad protein determination kit).

Determination of cytotoxicity is done using MTT (3-(4, 5-dimethylthiazol-2-yl)-2,5-diphenyl-tetrazolium bromide) assay.

Results

Adherent Cells a) Compound (1). The transfection efficiency of compound (1) on HeLa cells in the presence or absence of serum was compared to DOTAP. $5 \times 10^4$ cells per well (24-well plate) in 1 ml of complete RPMI 1640 were plated one day before transfection. Just before transfection, the medium was removed and cells were supplied with 1 ml fresh medium with or without serum. To assess the optimum ratio between cationic lipids and DNA, various quantities of both lipids in the transfection buffer (final volume 100 μl) were mixed with 100 μl of DNA solution containing 1 μg of pCMVL. After incubation for 10 min at room temperature 100 μl of this mixture containing 0.5 μg of the plasmid and half of the indicated amount of lipid was added to each well. In the presence of serum, plates were incubated for 24 hours without exchange of medium. In the absence of serum, the transfection medium was removed after 4 hours, and the cells were supplied with 1 ml fresh serum supplemented medium.

The cells were harvested for luciferase assay 24 hours after transfection as described above. The results are plotted in FIG. 2 as the total amount of a cationic lipid per 1 μg of PCMVL. In the case where cells were transfected in the presence of serum, the optimum expression of luciferase activity was obtained using DOTAP/DNA ratio of 10:1 (w/w) and a ratio of compound (1)/DNA of 5:1 (w/w), respectively. In the absence of serum, the optimum expression of luciferase activity of both lipids was obtained using a lipid/DNA ratio of 5:1 (w/w). Compound (1) mediated transfection, in comparison to DOTAP transfection, was 12-fold and 6-fold higher in presence and in absence of serum, respectively.

b) Ternary complex of compound (1). $5 \times 10^4$ cells per well in 1 ml of complete RPMI 1640 were plated one day before transfection. Just before transfection, the medium was removed and cells were supplied with 1 ml fresh medium with or without serum. To assess the influence of the HBV peptide on transfection of HeLa cells, various quantities of the peptide were mixed with 1 μg of pCMVL to make the final volume 100 μl, and incubated for 10 min. Then 100 μl of a solution containing 7.5 μg of compound (1) was added with mixing. After additional incubation for 10 min 100 μl of the transfection solution (containing 0.5 μg of DNA and 3.75 μg of compound (1)) was applied to the cells. After 4 hours transfection medium has been replaced with 1 ml of fresh complete growth medium.

24 hours after transfection cells were lysed and cell extracts were analysed for gene expression as described above. Transfection levels (with the transfection in the presence of serum) are plotted in FIG. 3 as a percentage of the value obtained with DOTAP transfection. The results show that the optimum amount of the peptide in these experiments was 5 μg, and that the expression of the luciferase activity was 14-fold and 200-fold higher than those achieved with compound (1) and DOTAP transfections, respectively. In the case of the transfection performed under serum free conditions, the optimum amount of the peptide was the same and the expression of the luciferase activity was about 10-fold higher than those achieved with compound (1) and 150-fold higher than with DOTAP transfections, respectively (data not shown).

c) Time dependence. $5 \times 10^4$ HeLa cells per well (24-well plate) in 1 ml of complete RPMI 1640 were plated one day before transfection. Just before transfection, the medium was removed and cells were supplied with 1 ml fresh medium with serum. 50 μl of the transfection solution containing 0.25 μg of pCMVLuc, 0.5 μg of HBV-peptide and 1.87 μg of compound (1) were added to each well with mixing. After 2 hours transfection medium has been replaced with 1 ml of fresh complete growth medium. The cells were harvested for luciferase assay at the indicated time as described above. The results are plotted in FIG. 2c as the total luciferase activity per well. As can be seen, luciferase activity rapidly increases, reaching maximum at 12 to 16 hours. Already after 2 hours, $4.5 \times 10^4$ light units were obtained. The same luciferase activity was observed after 3 hours with compound (1) mediated transfection, and only after 5 to 6 hours after DOTAP mediated transfection.

Suspension Cells

α) Compound (1)

The transfection efficiency of compound (1) on K562 cells in the presence of serum was compared to DOTAP. To assess the optimum ratio between cationic lipids and the DNA, various quantities of both lipids were added to a given amount of pCMVL (1 μg per well, or per $0.5 \times 10^6$ cells in 2 ml of the complete RPMI 1640, 24-well plates). 200 μl of the transfection mixture was added into each well and the plate was incubated for 24 h at 37° C. (one-step transfection). Cells were lysed as described above. The results are plotted in FIG. 4 as the total luciferase activity per well versus the amount of cationic lipid per 1 μg DNA. The optimum expression of luciferase activity was obtained using a DOTAP/DNA ratio of 5:1 (w/w) and compound (1)/DNA ratio of 7.5:1 (w/w). The obtained ratio corresponds to the charge ratio of lipid to DNA about 2:1 and 5:1 for DOTAP and compound (1), respectively (with the assumption that 1 μg of DNA contains 3.1 nm phosphate anionic charges). Compound (1) mediated transfection was more than 10-fold higher than those obtained with DOTAP.

B) Ternary Complex of Compound (1)

To assess the influence of peptide concentration on the transfection of K562 cells, various quantities of HBV-peptide were mixed with 1 μg of pCMVL to make the final volume 100 μl, and incubated for 10 min. Then 100 μl of a solution containing 10 μg of compound (1) was added with mixing. After additional incubation for 10 min the transfection solution (200 μl) was applied to the cells. All other conditions were exactly the same as described in the previous experiment. The results are shown in FIG. 5 as the total luciferase activity per well versus the amount of added peptide (per 1 μg DNA). The results show that the optimum amount of the peptide was 2 μg, and that the expression of the luciferase activity was 3- to 4-fold higher than those achieved with compound (1) and 30- to 40-fold higher than with DOTAP transfections, respectively.

γ) Dose Dependency

A "stock" solution was made from 1 μg of PCMVL, 2 μg HBV-peptide and 10 μg compound (1) in the final volume of 200 μl. The DNA dose dependency was checked in one-step transfection by adding from 5 to 200 μl of this solution to the cells. Results from this experiment are plotted in FIG. 6. The expression of the luciferase activity was dependent on the amount of added DNA and was linear in the range from 0 to 0.25 μg of DNA. In principal, under these conditions as little as 0.5 ng of reporter DNA (without carrier DNA) could be detected. The obtained results also indicate that once formed, these ternary complexes are very stable and do not dissociate with dilution.

Intracellular Introduction of Oligonucleotides

EXAMPLE 5

Fluorescein labelled phosphotioate oligonucleotide (5'-ACT TGG ATA CGC ACG-fluorescein-3) (SEQ ID NO.1) was used to access the intracellular delivery and distribution of oligonucleotide in the presence and absence of compound (1).

HeLa cells (plated one day before the experiment, $2 \times 10^5$ cells per well, 6-well plate) were grown on glass microscope slides in 2 ml of RPMI 1640 supplemented with 10% FCS. Before the experiment, the medium was replaced with RPMI 1640 without serum.

Formation of oligonucleotide-compound (1) complexes was done as follows. 10 μg of phosphotioate oligonucleotide was dissolved in 90 μl of transfection buffer. 16 μg and 50 μg of compound (1) were diluted with transfection buffer to the final volume of 100 μl. The two solutions were mixed together and incubated for 10 min. Oligonucleotide solution without compound (1) was diluted with 100 μl of transfection buffer. The resultant solutions (200 μl per well) were added to the cell cultures (final concentration of oligonucleotide was about 1 μM, compound (1) 8 μM and 25 μM). The complexes were incubated with the cells for 4 hours. The medium was then substituted with a complete growth medium.

At 4 and 24 hours, cells were washed three times with PBS and fixed with 1% glutaraldehyde solution for 15 min. After fixation, cells were washed three times with PBS and mounted in glycerol mounting solution (10 mM phosphate, 150 mM NaCl, 70% glycerol, pH 7.5). The localization of fluorescein labelled phosphothioate oligonucleotide was determined by fluorescent microscopy, using a Zeiss fluorescent microscope.

Incubation of cells with 1 μM fluorescein labelled oligonucleotide resulted in a faint fluorescence both after 4 and 24 hours. In contrast, all cells incubated with 1 μM fluorescein labelled oligonucleotide in the presence of compound (1) exhibited very bright punktate fluorescence in the cytoplasm. After 24 hours the cells show very clear punktate fluorescence in the cytoplasm. The fluorescence intensity was higher in the presence of 25 μM compound (1).

Experiments performed in the presence of serum did not change the overall fluorescence and distribution of fluorescein labelled oligonucleotide.

Intracellular Introduction of Anionic Polypeptides

EXAMPLE 6

Fluorescein labelled anionic polypeptide (fluoresceinpoly $(Glu)_{21}$) (SEQ ID NO:2) was used to access the intracellular delivery and distribution of anionic polypeptide in the presence and absence of compound (1). Conditions of the experiment were exactly the same as described in the previous example.

Incubation of cells with 1 μM fluorescein labelled poly-$(Glu)_{21}$ did not result in fluorescence neither after 4 nor 24 hours. In contrast, all cells incubated with 1 μM fluorescein labelled oligonucleotide in the presence of 25 μM compound (1) exhibited bright cytoplasmic punktate fluorescence already after 45 min. The localization of the fluorescence vesicles was somehow different form those observed with fluorescein labelled oligonucleotide. After 24 hours cells exhibited very bright punktate fluorescence in the cytoplasm, most likely localized within the same structures.

EXAMPLE 7

Liposome Formulations

The following compositions illustrate the use of compounds according to the present invention in formulations comprising biologically active agents:

7.1 A topical formulation was prepared by dissolving 0.25 mg of prednisolone acetate (21-acetoxy-1,4-pregnadien-11β, 17a-diol-3,20-dion) and 50 mg of L-lysine-bis-(O,O'-oleoyl-β-hydroxyethyl) amide dihydrochloride in 2 ml of dichloromethane:ethanol (1:1) solution. The solvent was evaporated under a stream of nitrogen. The film mixture was placed under vacuum overnight to vaporate off the residual solvent completely. The dry film was then suspended in 2 ml of 0.9% NaCl solution. The solution was sonicated until visually clear.

7.2 (+)-α-tocopherol (5,7,8-trimethyltocol, vitamin E) and 100 mg of L-lysine-bis-(O,O'-oleoyl-β-hydroxyethyl) amide dihydrochloride were dissolved in 5 ml of dichloromethane:ethanol (1:1) solution. The solvent was evaporated under a stream of nitrogen and the residual was evaporated off under vacuum. The dry film was then suspended in 4 ml of 10 mM Hepes, 0.9% NaCl, pH 7.4, and sonicated until visually clear.

7.3 20 mg retinol (3,7-dimethyl-9-(2,6,6-trimethyl-1-cyclo-hexenyl)-2,4,6,8-nonatetraen-1-ol) and 80 mg of L-lysine-bis-(O,O'-myristoyl-β-hydroxyethyl)amide dihydrochloride were dissolved in 5 ml of dichloromethane:ethanol (1:1) solution. The solvent was evaporated and the dry film was placed under vacuum overnight. The film was then suspended in 5 ml of 10 mM Tris, 0.9% NaCl, pH 7.4.

7.4 3 mg N-palmitoyl-S(2,3-bis(palmitoyl-oxy)-(2RS)-propyl-R-cystein and 25 mg of L-lysine-bis-(O,O'-palmitoyl-β-hydro-xyethyl)amide dihydrochloride were dissolved in 5 ml of dichloromethane:ethanol (1:1) solution and evaporated under vacuum until dryness. The resulting film was suspended in 1 ml of distilled water and treated with ultrasound until clear.

Besides the portions described so far, the present invention also comprises the use of lipid compounds according to the invention for the introduction of lipophilic portions into peptides as well as the lipopeptides produced in this manner. Further details will become apparent from the following:

Peptide Synthesis
General Procedure the synthesis of peptides having lipophilic modifications at their C- or N-terminus, or both, or within the chain, was accomplished by all-stepwise solid phase Fmoc-based synthetic methods using automated peptide synthesizer ABI 350 or multiple peptide synthesizer.

Peptides were usually assembled on a Rink amide MBHA resin (4-(2',4'-dimethoxyphenyl-Fmoc-aminomethyl) phenoxyacetamido-norleucyl-methylbenzhydrylamin resin, Novabiochem) or on a trityl resin (2-chlorotritylchloride resin, Novabiochem).

The couplings of the Fmoc-amino acids (10 molar excess) were performed with N-N'-diisopropylcarbodiimide (DIC) and 1-hydroxybenzotriazole (HOBt) in DMF usually for about one hour. The couplings of the lipophilic amino acid-bis-hydroxyethyl amides were achieved using their three molar excess, the same DIC/HOBt activation method and a coupling time for about 3 hours. The completeness of coupling was monitored with a ninhydrin test. The Fmoc group was removed with piperidine:DMF=1:2 within 15 min.

Cleavage and final deprotection was performed with a mixture of n-cresol:dimethylsulfide:ethanediol:TFA=3:3:3:91 for two hours at room temperature. After filtration, peptides were precipitated from the mixture and washed several times with diethyl ether. The crude peptides were purified on a semipreparative Nucleosil C2 column (8×250 mm) and an ascending gradient of acetonitrile in water, each containing 0.1% of TFA. Purified peptides were lyophilized from the mixture of tert-butyl alcohol:water=4:1 and stored at −4° C. Their homogeneitiy was verified by amino acid analysis, analytical HPLC and electrospray-ionization mass spectrometry.

According to this procedure the following lipopeptides were prepared:

GLFGAIAAGFIENGWEGLIDG-D(N(EtOPalm)$_2$)-NH$_2$ (SEQ ID NO: 3)

E(N(EtOPalm)2)-MQRGNFRNQRKMVKGGRAPRKKG (SEQ ID NO: 4)

E(N(EtOMyr)2)-MQRGNFRNQRKMVKGGRAPRKKG (SEQ ID NO: 5)

GRGDSPGSG-D(N(EtOPalm)2)-NH$_2$ (SEQ ID NO: 6)

Acetyl-GRGDSPGSG-D(N(EtOPalm)$_2$)-NH$_2$ (SEQ ID NO: 7)

YNRNAVPNLRGDLQVLAQKVARTL-E(N(EtOPalm)$_2$-NH$_2$ (SEQ ID NO:8)

E(N(EtOPalm)$_2$-YNRNAVPNLRGDLQVLAQKVARTL-E(N(EtOPalm)$_2$-NH$_2$ (SEQ ID NO:9)

YPS-E(N(EtOPalm)$_2$-PDNPGEDAPAEDMARYYSALRHYINLITRQRY-NH$_2$ (SEQ ID NO:10)

Further the invention comprises the use of lipid compounds according to the invention for the introduction of glycolipophilic portions into peptides as well as glycolipopeptides produced in this manner. Further details will become apparent from the following:

Synthesis of Glyco-Lipopeptides
Lys(NH-Asn(Lactosyl))$_4$-Lys$_2$-Lys-Acx-bAla-Acx-E(N(EtOPalm)$_2$-NH$_2$ 1.8 g (5 mmol) of D(+)-lactose monohydrate was reacted with 40 ml of saturated NH$_4$HCO$_3$ for 6 days at 30° C. To remove the excess of NH$_4$HCO$_3$, the reaction mixture was diluted with water (20 ml) and concentrated in vacuo to half of its original volume. This procedure was repeated 6 times. Finally, the water was removed by lyophilization. The resulting crude amino sugar was used without further purifiaction for the synthesis of Fmoc-Asn(lactose)-OtBu derivatives. 480 mg (1.17 mmol) of Fmoc-Asp-OtBu and 228 mg (1.52 mmol) of HOBt were idssolved in DMF (5 ml) and after cooling to 4° C., 205 mg (1.63 mmol) of DIC was added. After stirring at 4° C. for 15 min and at 25° C. for 20 min, 5.85 mmol crude 1-amino lactose was added to the active ester in 6 ml of DMF:H$_2$O=2:1. After stirring for 6 hours the solvent was evaporated in vacuo and diethylether was added. The precipitated product was filtered, washed with cold ether and cold water. The tBu-protecting group was cleaved by 70% TFA in water (20 min at room temperature). After evaporating of the TFA/water mixture in vacuo, the product was dissolved in tert-butyl alcohol:water=4:1 and lyophilized. Crude Fmoc-Asn(lactose)-OH was purified by reversed-phase chromatography (Lichroprep C18 column 25×310 mm, isocratic elution at 30% acetonitrile/-water/0.1% TFA) to give 280 mg of HPLC pure Fmoc-Asn(lactose)-OH (yield 35% based on starting Fmoc-Asp-AtBu. Analysis: +FAB-MS (MH+)=679 (calculated=679), Rt=6.59 min on Nucleosil C18 4×150 mm, gradient 30 to 100% of acetonitrile/0.1% TFA in water/0.1% TFA in 30 min).

32.5 mg (0.048 mmol) of Fmoc-Asn(lactose)-OH and 7.25 mg (0.05 mmol) HOBt were dissolved in 200 μl of DMF and 6.31 mg (0.05 mmol) DIC was added. After stirring for 30 min the formed active ester was coupled overnight to 30 mg (0.016 mmol) of Boc-(Lys(NH$_2$))$_4$-Lys$_2$-Lys-Acx-bAla-Acx-E(N(EtOPalm)$_2$)-peptidyl resin. The resin was carefully washed and the Fmoc group was removed with 20% piperidine treatment. The glycopeptide was cleaved of, deprotected and worked up under identical conditions as described above. Finally, it was purified by semipreparative HPLC to give 10.6 mg of N-lactosylated lipopeptide.

SEQUENCE LISTING

Figure 1:
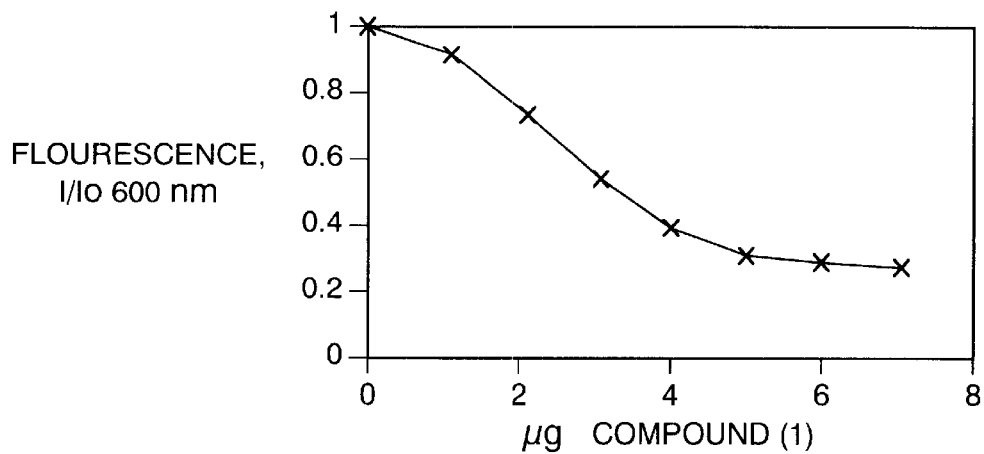
FIG. 1 of the accompanying illustrations shows the fluorescence intensity as a function of the amount of compound (1) added.
Figure 2:
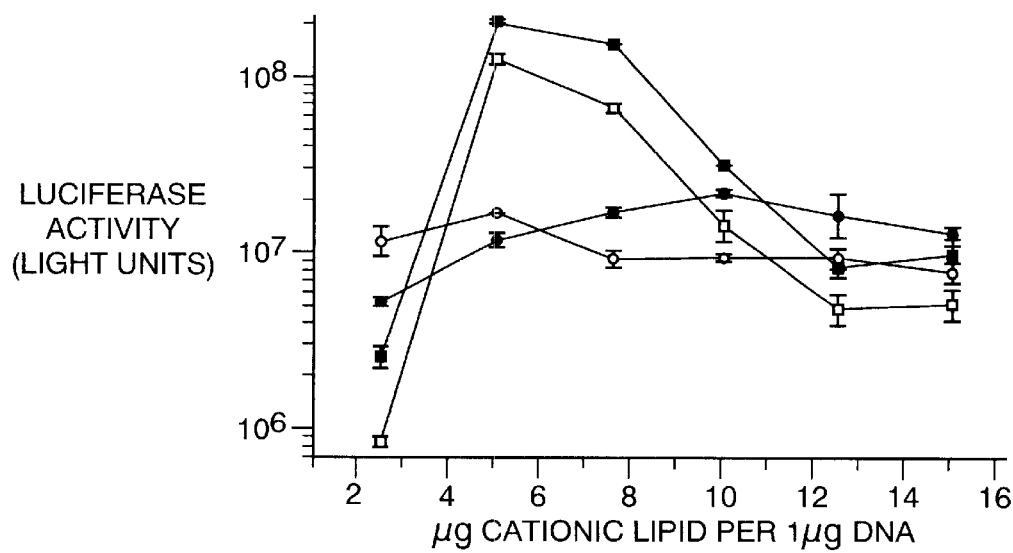
FIG. 2 shows the effect of the ratio of DOTAP/DNA and compound (1)/DNA on the transfection of HeLa cells. The transfection of compound (1) is illustrated in the presence (■) and in the absence (□) of serum. The DOTAP transfection is illustrated in the presence (●) and in the absence (○) of serum. Transfection levels are given as total light units per 50000 cells. Each point is to represent the mean±SD of triplicate transfection.
Figure 3:
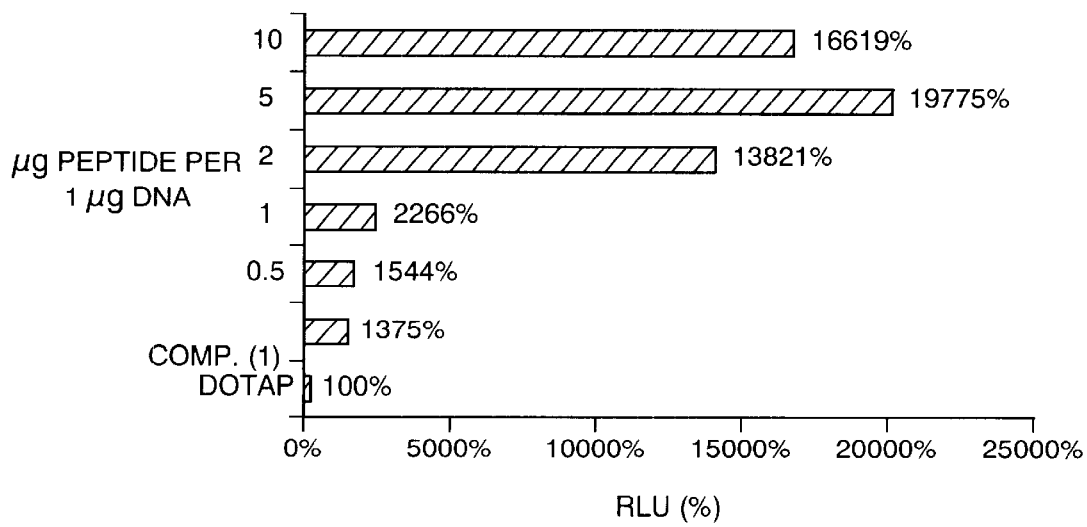
FIG. 3 illustrates peptide enhanced gene transfer to HeLa cells. Transfection levels are given as percentages of the value obtained with DOTAP transfection and show the mean of triplicate transfection.
Figure 4:
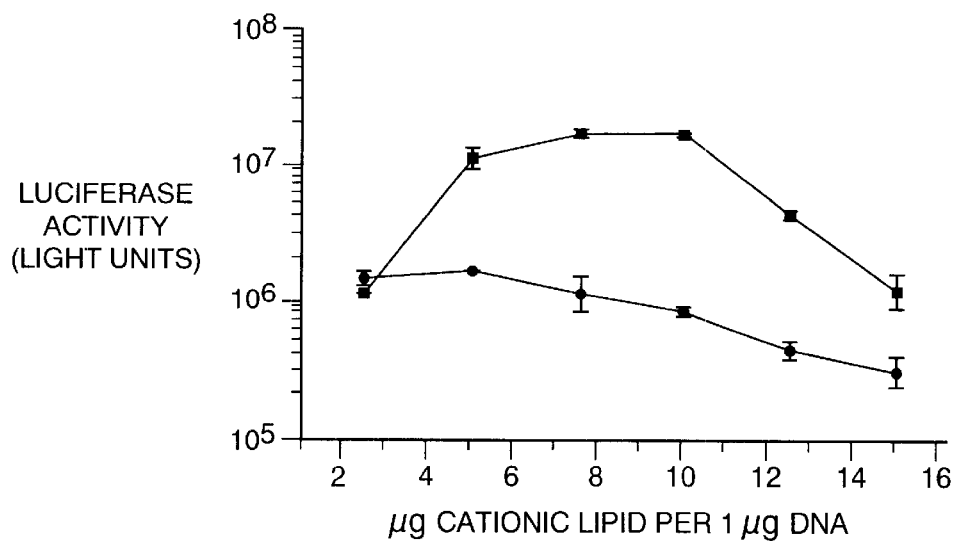
FIG. 4 illustrates the effect of the ratios DOTAP (●)/DNA and compound (1) (■)/DNA on transfection of K562 cells. Transfection levels are given as total light units per 500000 cells. Each point is to represent the mean±SD of triplicate transfection.
Figure 5:
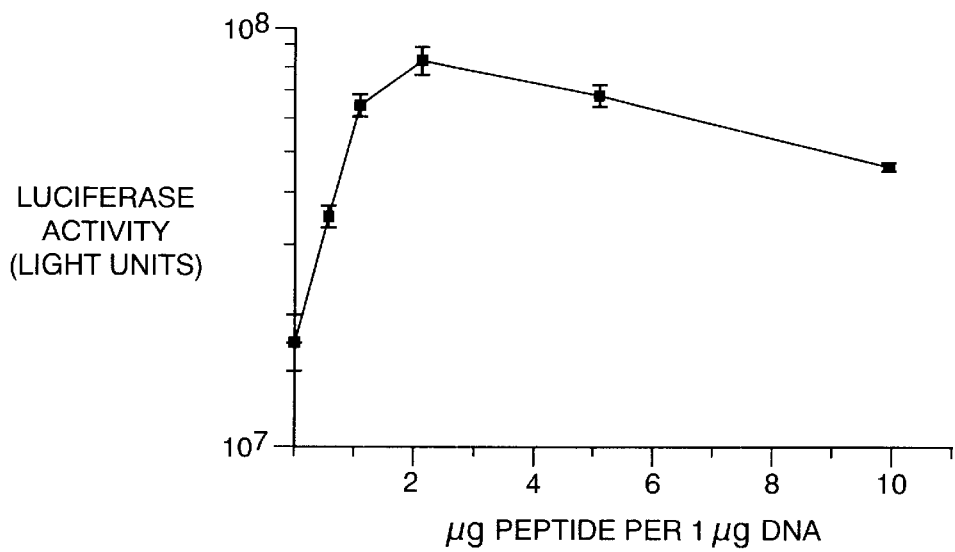
FIG. 5 illustrates peptide enhanced gene transfer to K562 cells. Transfection levels are given as total light units per 500000 cells and show the mean±SD of triplicate transfection.
Figure 6:
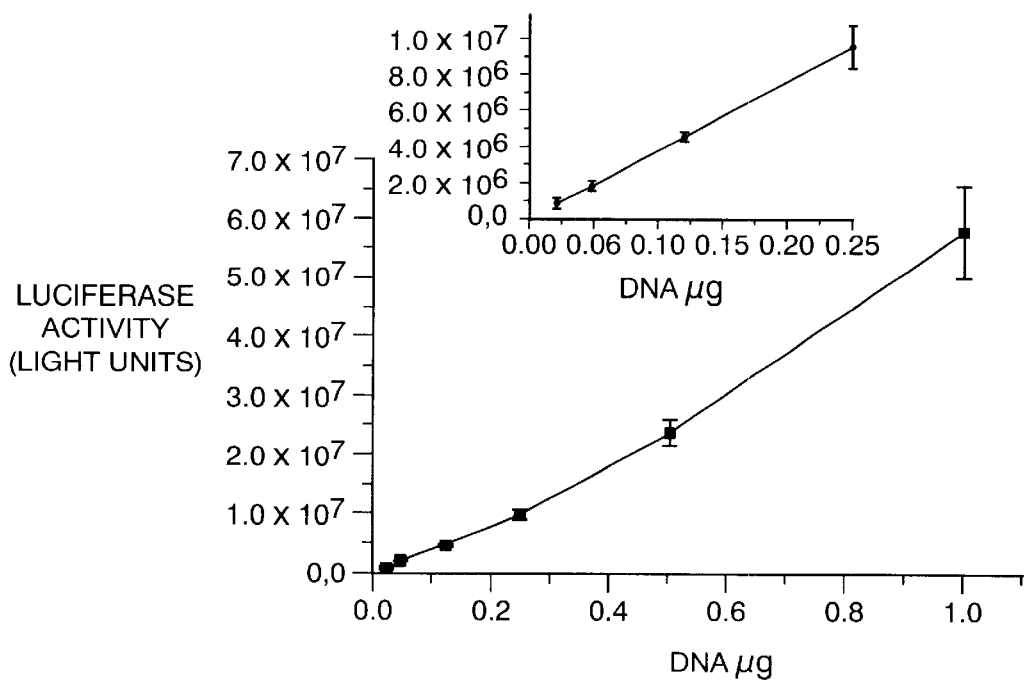
FIG. 6 illustrates transfection levels versus the amount of added DNA. Transfection levels are given as total light units per 500000 cells and show the mean±SD of triplicate transfection.

```
<160> NUMBER OF SEQ ID NOS: 15

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: labeled
      oligonucleotide

<400> SEQUENCE: 1
acttggatac gcacg                                                    15

<210> SEQ ID NO 2
<211> LENGTH: 21
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 2

Glu Glu Glu Glu Glu Glu Glu Glu Glu Glu Glu Glu Glu Glu Glu Glu
 1               5                  10                  15

Glu Glu Glu Glu Glu
            20

<210> SEQ ID NO 3
<211> LENGTH: 21
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 3

Gly Leu Phe Gly Ala Ile Ala Ala Gly Phe Ile Glu Asn Gly Trp Glu
 1               5                  10                  15

Gly Leu Ile Asp Gly
            20

<210> SEQ ID NO 4
<211> LENGTH: 23
<212> TYPE: PRT
<213> ORGANISM: Artificial Sequence
<220> FEATURE:
<223> OTHER INFORMATION: Description of Artificial Sequence: synthetic
      polypeptide
```

```
<400> SEQUENCE: 4

Met Gly Arg Gly Asn Phe Arg Asn Gln Arg Lys Met Val Lys Gly Gly
 1               5                  10                  15

Arg Ala Pro Arg Lys Gly
             20

<210> SEQ ID NO 5
<211> LENGTH: 23
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 5

Met Gln Arg Gly Asn Phe Arg Asn Gln Arg Lys Met Val Lys Gly Gly
 1               5                  10                  15

Arg Ala Pro Arg Lys Gly
             20

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 6

Gly Arg Gly Asp Ser Pro Gly Ser Gly
 1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 7

Gly Arg Gly Asp Ser Pro Gly Ser Gly
 1               5

<210> SEQ ID NO 8
<211> LENGTH: 24
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 8

Tyr Asn Arg Asn Ala Val Pro Asn Leu Arg Gly Asp Leu Gln Val Leu
 1               5                  10                  15

Ala Gln Lys Val Ala Arg Thr Leu
             20

<210> SEQ ID NO 9
<211> LENGTH: 24
<212> TYPE: PRT
<213> ORGANISM: Artificial Sequence
<220> FEATURE:
<223> OTHER INFORMATION: Description of Artificial Sequence: synthetic
      polypeptide
```

```
<400> SEQUENCE: 9

Tyr Asn Arg Asn Ala Val Pro Asn Leu Arg Gly Asp Leu Gln Val Leu
 1               5                  10                  15

Ala Gln Lys Val Ala Arg Thr Leu
            20

<210> SEQ ID NO 10
<211> LENGTH: 32
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 10

Pro Asp Asn Pro Gly Glu Asp Ala Pro Ala Glu Asp Met Ala Arg Tyr
 1               5                  10                  15

Tyr Ser Ala Leu Arg His Tyr Ile Asn Leu Ile Thr Arg Gln Arg Tyr
            20                  25                  30

<210> SEQ ID NO 11
<211> LENGTH: 26
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 11

Gly Arg Ser Pro Arg Arg Arg Thr Pro Ser Pro Arg Arg Arg Arg Ser
 1               5                  10                  15

Gln Ser Pro Arg Arg Arg Arg Ser Gln Ser
            20                  25

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 12

Arg Arg Arg Arg Ser Gln Ser Pro Arg Arg Arg Arg Ser Gln Ser
 1               5                  10                  15

<210> SEQ ID NO 13
<211> LENGTH: 36
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 13

Pro Lys Lys Lys Arg Lys Val Pro Gly Ser Gly Arg Ser Pro Arg Arg
 1               5                  10                  15

Arg Thr Pro Ser Pro Arg Arg Arg Arg Ser Gln Ser Pro Arg Arg Arg
            20                  25                  30

Arg Ser Gln Ser
            35

<210> SEQ ID NO 14
<211> LENGTH: 26
```

```
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 14

Pro Lys Lys Lys Arg Lys Val Pro Gly Ser Gly Arg Arg Arg Arg Ser
 1               5                  10                  15

Gln Ser Pro Arg Arg Arg Arg Ser Gln Ser
            20                  25

<210> SEQ ID NO 15
<211> LENGTH: 26
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 15

Gly Arg Ala Pro Arg Arg Arg Thr Pro Ala Pro Arg Arg Arg Arg Ala
 1               5                  10                  15

Gln Ala Pro Arg Arg Arg Arg Ala Gln Ala
            20                  25
```

What is claimed is:

1. A compound according to the formula:

$$R_4-\overset{R_3}{\underset{R_5}{\overset{|}{\underset{|}{N^+}}}}-\overset{}{\underset{W}{\overset{|}{\underset{|}{CH}}}}-Y-N\overset{(CH_2)_{\overline{n}}-Z-R_1}{\underset{(CH_2)_{\overline{n}}-Z-R_2}{\diagdown}} \quad X^-$$

or an optical isomer thereof, wherein $R_1$ and $R_2$ are the same or different and are an alkyl, alkenyl, or alkynyl group of 6 to 24 carbon atoms;

$R_3$, $R_4$, and $R_5$ are the same or different and are hydrogen, alkyl or alkylamine, having in each case from 1 to 8 carbon atoms or an amino acid, or peptide;

W is a side chain group of a basic amino acid;

Y is a linking group having at least one atom other than hydrogen;

Z is an ester, ether, or amide bond;

n is from 1 to 8; and

X is a pharmaceutically acceptable anion.

2. The compound according to claim 1 wherein Y is selected from the group consisting of, —CO—, —(CH$_2$)$_m$CO—, —(CH$_2$—)$_m$, —(CHOHCH$_2$—)$_m$, wherein m is from 1 to 20, —CH$_2$—S—CH$_2$—, —CH$_2$—SO—CH$_2$—, —CH$_2$—SO$_2$—CH$_2$—, —CH$_2$—SO$_2$—or —SO$_2$—.

3. The compound according to claim 1, wherein Y is carbonyl.

4. The compound according to claim 1 wherein Z is an ester bond.

5. The compound according to claim 1, wherein $R_1$ and $R_2$ are the same or different and are an alkyl or an alkenyl group having from 10 to 20 carbon atoms.

6. The compound according to claim 5 wherein $R_1$ and $R_2$ are the same or different and are an alkyl or an alkenyl group having from 12 to 18 carbon atoms.

7. The compound according to claim 1, wherein $R_1$ and $R_2$ are an alkenyl group.

8. The compound according to claim 1, wherein n is 2.

9. The compound according to claim 1, wherein W is a side chain group of lysine or ornithine.

10. The compound according to claim 1, wherein $R_3$, $R_4$, and $R_5$ are hydrogen.

11. The compound according to claim 1, wherein $X^-$ is a chloride anion.

12. The compound according to claim 1, wherein the compound is selected from the group consisting of:

L-Lysine-bis-(O, O'-cis-9-octadecenoyl-β-hydroxyethyl)-amide dihydrochloride or an optical isomer thereof, L-Lysine-bis-(O, O'-hexadecanoyl-β-hydroxyethyl) amide dihydrochloride or an optical isomer thereof, L-Ornithine-bis-(O, O'-cis-9-octadecenoyl-β-hydroxyethyl) amide dihydrochloride or an optical isomer thereof, L-Ornithine-bis-(O, O'-hexadecanoyl-β-hydroxyethyl) amide dihydrochloride or an optical isomer thereof, L-Lysine-bis-(O, O'-tetradecenoyl-β-hydroxyethyl) amide dihydrochloride or an optical isomer thereof, and L-Ornithine-bis-(O, O'-tetradecenoyl-β-hydroxyethyl) amide dihydrochloride or an optical isomer thereof.

13. The compound according to claim 12, wherein the compound is L-Lysine-bis-(O, O'-cis-9-octadecenoyl-β-hydroxyethyl) amide dihydrochloride or an optical isomer thereof.

14. A polyanion-lipid complex composed of a polyanion and at least one compound according to any of the claims 1 to 13.

15. The complex according to claim 14, having a positive total or net charge.

16. The complex according to claim 14, wherein the polyanion is a polynucleotide.

17. The complex according to claim 16, wherein the polyanion is DNA or RNA.

18. The complex according to claim 14, wherein the polyanion is a polypeptide.

19. The complex according to claim 14, wherein the lipid is the compound according to claim 13 or an optical isomer thereof.

20. A ternary polyanion-polycation-lipid complex composed of a polyanion, a polycation, and at least one compound according to any of the claims 1 to 13.

21. The complex according to claim 20, having a positive total or net charge.

22. The complex according to claim 20, wherein the polyanion is a polynucleotide.

23. The complex according to claim 22, wherein the polyanion is DNA or RNA.

24. The complex according to claim 20, wherein the polycation is a polypeptide.

25. The complex according to claim 24, wherein the polypeptide comprises at least one of the following amino acid sequences:

a) GRSPRRRTPSRRRRSQSPRRRRSQS (SEQ ID NO:11),
  b) RRRRSQSPRRRRSQS (SEQ ID NO:12),
  c) PKKKRKVPGSGRSPRRRTPSPRRRR-SQSPRRRRSQS (SEQ ID NO:13),
  d) PKKKRKVPGSGRRRRSQSPRRRRSQS (SEQ ID NO:14),
  e) GRAPRRRTPAPRRRRAQAPRRRRAQA (SEQ ID NO:15),
  f) a protamine sequence,
  g) a histone sequence.

26. The complex according to claim 20, wherein the compound is L-Lysine-bis-(O, O'-cis-9-octadecenoyl-β-hydroxyethyl) amide dihydrochloride or an optical isomer thereof.

27. A method for the preparation of a polyanion-lipid complex, comprising the step of contacting at least one positively charged compound according to any of claims 1 to 13, or a composition including at least one such compound, with a polyanion.

28. A method for the preparation of a ternary polyanion-polycation lipid complex comprising the steps of:

(a) contacting a polyanion and a polycation to form a polyanion-polycation complex, and
  (b) contacting the complex of step (a) with at least one positively charged compound according to any of claims 1 to 13, or a composition including such compound.

29. A liposome prepared with at least one compound according to any of claims 1 to 13.

30. A liposome formulation including:

at least one biologically active substance, and
  a lipid component, including at least one compound according to any of claims 1 to 13.

31. The liposome formulation according to claim 30, wherein the biologically active substance is present in an amount up to 10% by weight.

32. The liposome formulation according to claim 30, wherein the lipid component is present in an amount from 1 to 20% by weight.

33. The liposome formulation according to claim 30, wherein the compound in the lipid component constitutes from 1% to 100% of the component.

34. The liposome formulation according to claim 30, wherein the biologically active substance is a drug.

35. A method for the transport of a polyanion and/or a polycation through a biological membrane comprising, (a) contacting the polyanion and/or the polycation with at least one compound according to any of claims 1 to 13 to form a ternary complex and
  (b) contacting the formed complex with the membrane.

36. The method according to claim 35 wherein said biological membrane is a cell membrane and the polyanion or polycation is transported through said cell membrane and into said cell.

37. The method according to claim 35 further comprising, (c) incubating said cell with said complex.

38. The method according to claim 35, wherein the complex has a positive total or net charge.

39. The method according to claim 35, wherein the complex is a complex formed according to any of claims 14 to 19.

40. The method according to claim 35, wherein the complex is a complex formed according to any of claims 20 to 26.

41. The method according to claim 35, wherein the contacting of step (b) is performed in vitro.

42. The method according to claim 35, wherein the contacting of step (b) is performed in vivo.

43. The method according to claim 41 wherein the contacting includes incubating the liposome with the membrane and the biological membrane is a cell membrane.

44. The method according to claim 42 wherein the contacting includes incubating the liposome with the membrane and the biological membrane is a cell membrane.

45. A method for the transport of a biologically active substance through a biological membrane comprising, (a) forming a liposome by complexing at least one compound according to any of claims 1 to 13 with a biologically active substance, and
  (b) contacting the liposome with the membrane.

46. The method according to claim 45 wherein said biological membrane is a cell membrane and the liposome is transported through said cell membrane and into said cell.

47. The method according to claim 45 or 46 further comprising, (c) incubating said cell with said liposome.

48. The method according to claim 45, wherein the biologically active substance is a drug.

49. The method according to claim 45, wherein the contacting is performed in vitro.

50. The method according to claim 45, wherein the contacting is performed in vivo.

51. The method according to claim 49 wherein the contacting includes incubation and the biological membrane is a cell membrane.

52. The method according to claim 50 wherein the contacting includes incubation and the biological membrane is a cell membrane.

* * * * *

UNITED STATES PATENT AND TRADEMARK OFFICE
CERTIFICATE OF CORRECTION

PATENT NO. : 6,458,381 B1  Page 1 of 1
DATED : October 1, 2002
INVENTOR(S) : Andrej Sourovoi and Guenther Jung It is certified that error appears in the above-identified patent and that said Letters Patent is hereby corrected as shown below:

<u>Column 29,</u>
Lines 18 and 19, delete "a) GRSPRRRTPSRRRRSQSPRRRRSQS (SEQ ID NO:11)", and insert therefor: --
-- a) GRSPRRRTPSPRRRRSQSPRRRRSQS (SEQ ID NO: 11) --

Signed and Sealed this

Twentieth Day of May, 2003

JAMES E. ROGAN
*Director of the United States Patent and Trademark Office*